(12) United States Patent
Dolinskii et al.

(10) Patent No.: US 6,476,403 B1
(45) Date of Patent: Nov. 5, 2002

(54) GANTRY WITH AN ION-OPTICAL SYSTEM

(75) Inventors: Alexeiy Dolinskii; Bernhard Franczak; Marius Pavlovic, all of Darmstadt (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 0 days.

(21) Appl. No.: 09/936,383

(22) PCT Filed: Apr. 3, 2000

(86) PCT No.: PCT/EP00/02948

§ 371 (c)(1),
(2), (4) Date: Dec. 11, 2001

(87) PCT Pub. No.: WO00/60611

PCT Pub. Date: Oct. 12, 2000

(30) Foreign Application Priority Data

Apr. 1, 1999 (EP) ............................................. 99106657

(51) Int. Cl.[7] ............................. H01J 3/32; G21G 1/10; G22G 1/10; A61N 5/00; H05H 9/00
(52) U.S. Cl. .................... 250/492.3; 250/398; 328/235; 315/501; 315/507

(58) Field of Search ................................ 250/281, 290, 250/291, 294, 295, 296, 297, 298, 396 R, 400, 492.21, 492.3, 496.1; 328/233, 234, 235; 315/501, 507

(56) References Cited

U.S. PATENT DOCUMENTS

| | | | | |
|---|---|---|---|---|
| 4,870,287 A | * | 9/1989 | Cole et al. ................ | 250/492.3 |
| 5,190,516 A | * | 3/1993 | Bronn .......................... | 600/1 |
| 5,260,581 A | * | 11/1993 | Lesyna et al. ........... | 250/492.3 |
| 5,585,642 A | * | 12/1996 | Britton et al. ........... | 250/492.3 |
| 6,034,377 A | * | 3/2000 | Pu .......................... | 250/492.3 |
| 6,316,776 B1 | * | 11/2001 | Hiramoto et al. ........ | 250/492.3 |
| 2002/0033456 A1 | * | 3/2002 | Tachikawa et al. ........ | 250/398 |

* cited by examiner

Primary Examiner—John R. Lee
Assistant Examiner—David A. Vanore
(74) Attorney, Agent, or Firm—Frommer Lawrence & Haug LLP; Ronald R. Santucci

(57) ABSTRACT

The present invention is drawn to a gantry for an ion-optical system comprising an ion source and three bending magnets for deflecting an ion beam about an axis of rotation. A plurality of quadrupoles are also provided along the beam path to create a fully achromatic beam transport and an ion beam with different emittances in the horizontal and vertical planes. Further, two scanning magnets are provided between the second and third bending magnets to direct the beam.

3 Claims, 6 Drawing Sheets

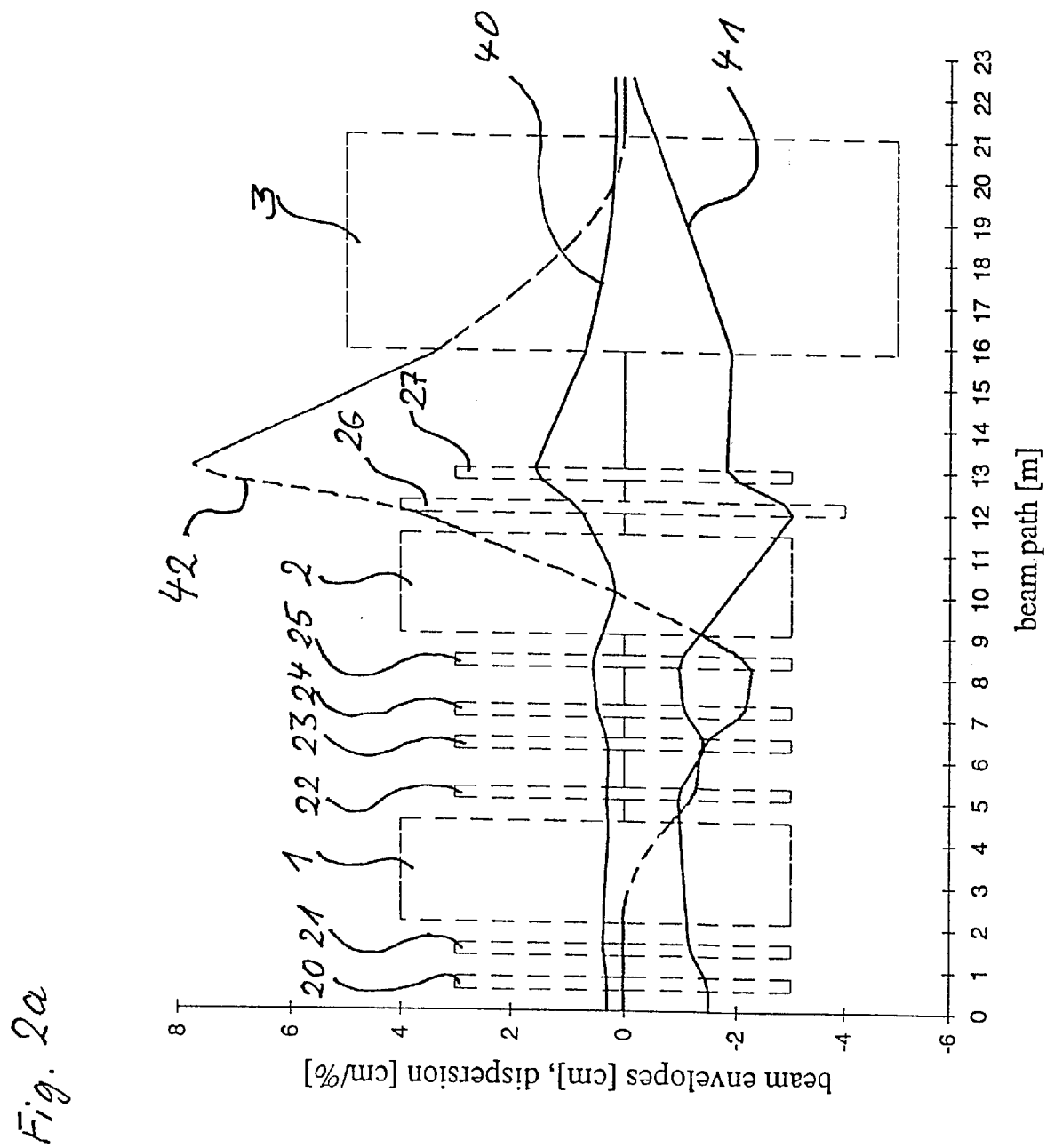

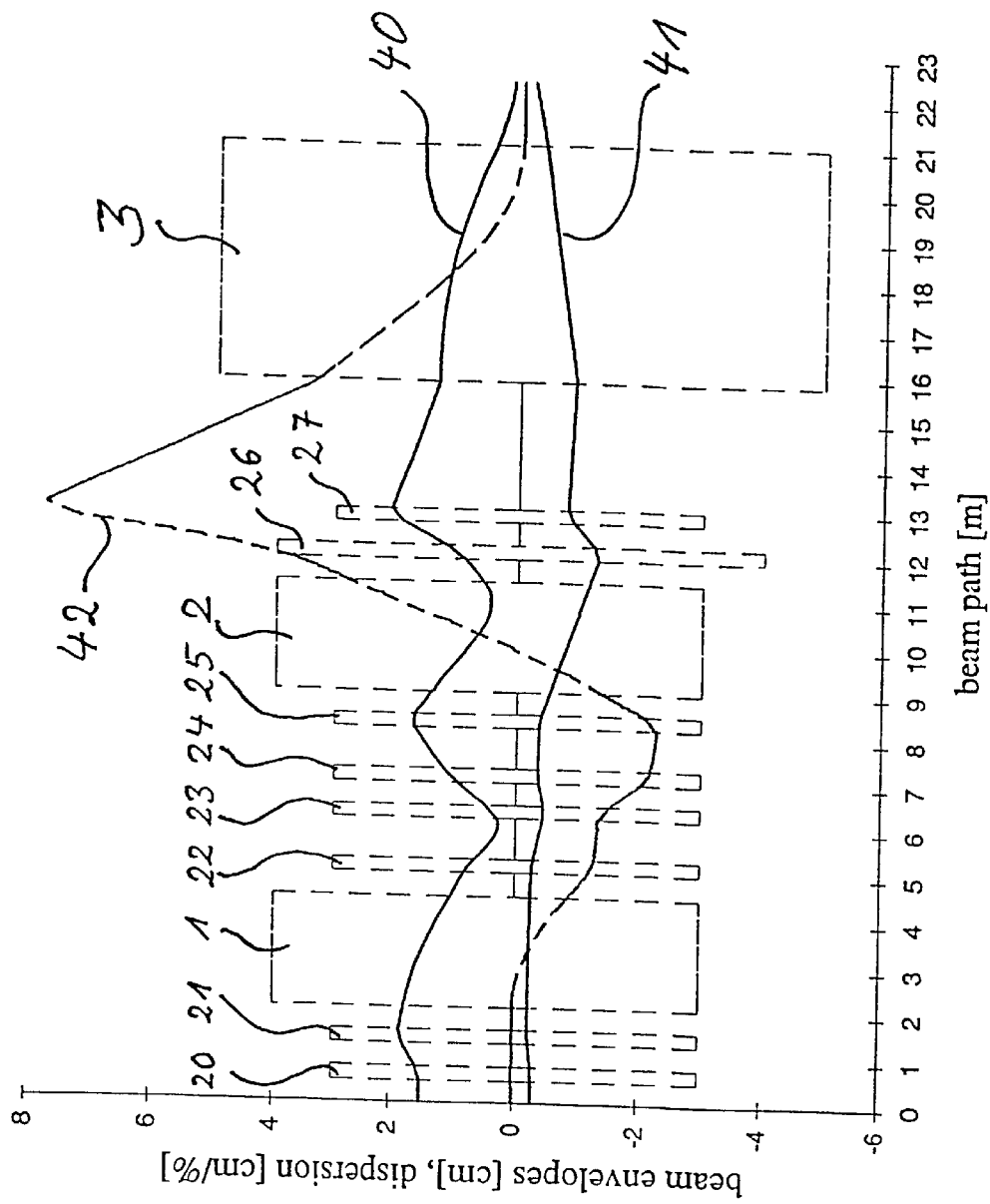

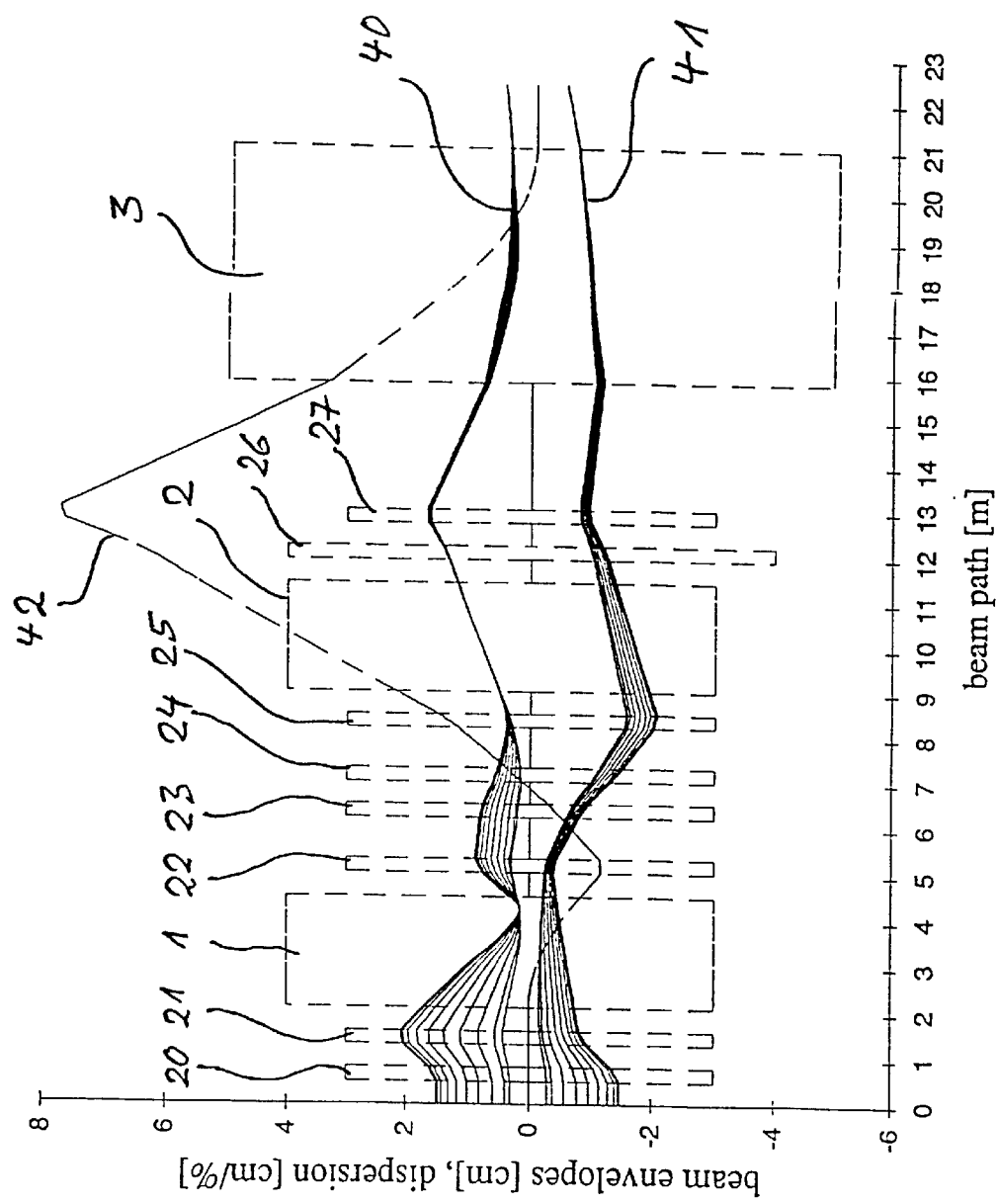

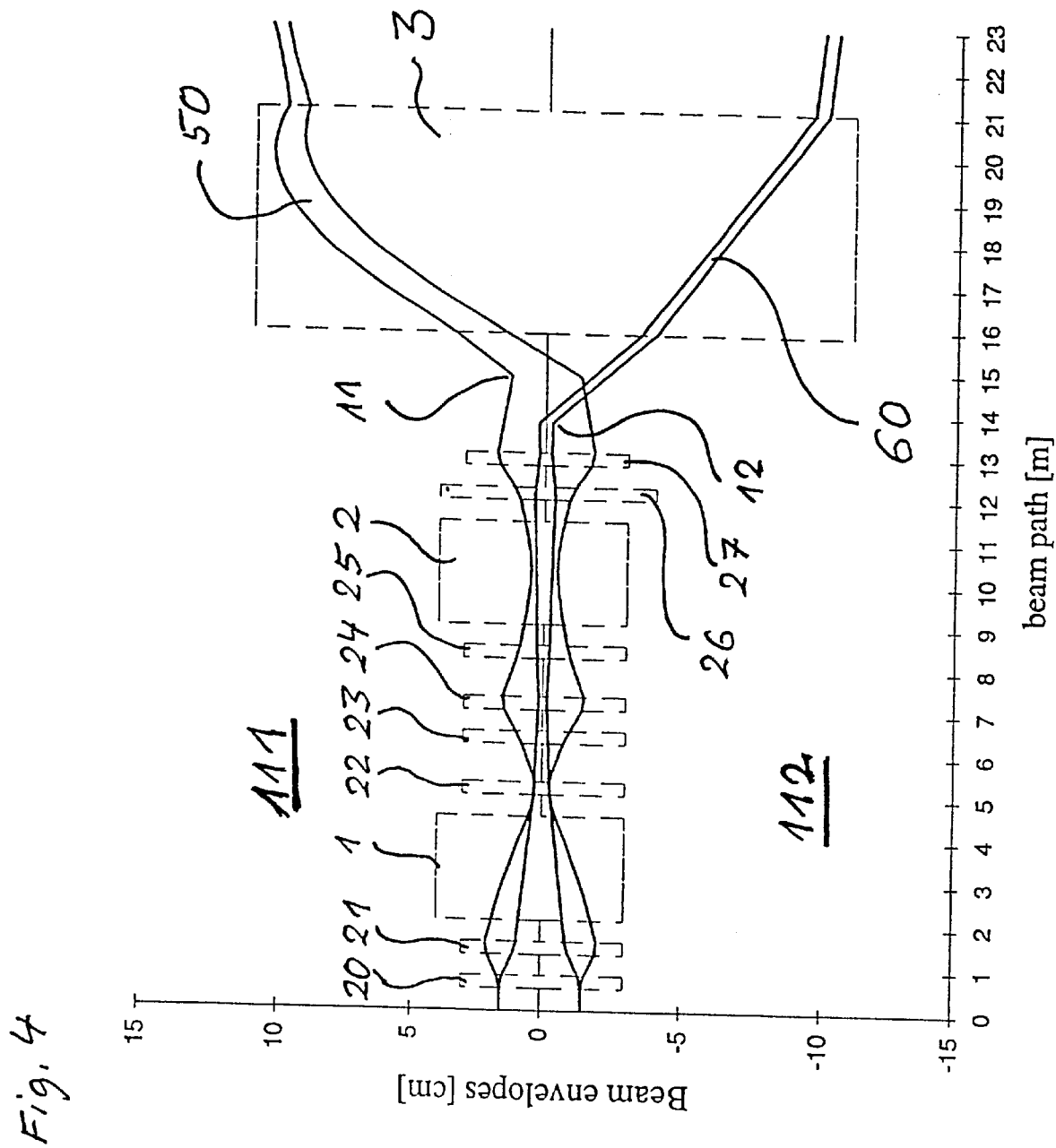

GANTRY WITH AN ION-OPTICAL SYSTEM

The present invention relates to a gantry with an ion-optical system according to the preamble of claim 1.

Such an ion-optical system for a gantry encloses a first bending magnet with a bending angle as known from U.S. Pat. No. 4,870,287 of 90° for bending a proton beam off an axis of rotation of said gantry. Further a second bending magnet with a bending angle identical to the bending angle of the first bending magnet bends said ion beam parallel to said axis of said gantry. Finally, a third bending magnet with a bending angle of 90° according to the above mentioned prior art bends said ion beam toward an intersection of said ion beam with said axis of rotation of said gantry. This intersection is called isocentre.

From U.S. Pat. No. 4,870,287 is further known, that between the first and the second bending magnet two quadrupole magnets are positioned. Also between the second and the third bending magnets two other quadrupole magnets are positioned. The disadvantage of such a gantry is, however, that if a non-symmetric ion beam is introduced to the gantry input from a fixed transfer line the beam transport within such a gantry having only four quadrupoles becomes dependent on the angle of gantry rotation, wherein the non-symmetric beam is ment as a beam having different emittances in vertical and horizontal planes.

Theoretical studies of medical synchrotrons as well as the measurements at existing facilities have shown that the slowly extracted beams do have the above mentioned different emittances in horizontal and vertical planes. This complicates the matching of the fixed transfer line to the rotating gantry. The input beam parameters in the horizontal and vertical planes of the gantry become a function of the angle of gantry rotation and this dependence, unless special precautions are applied, is transformed also to the beam parameters of the gantry exit.

To overcome these disadvantages a special matching section, called a "rotator" comprising additionally to the quadrupole magnets within the gantry a plurality of other quadrupole magnets was proposed by M. Benedikt and C. Carli, "Matching to gantries for medical synchrotrons", Particle Accelerator Conference PAC '97, Vancouver 1997. The rotator is positioned upstream the gantry within the fixed transfer line.

The rotator provides a universal method allowing to match the rotating gantries to the fixed transfer lines without applying any specific ion-optical constraints upon the gantries. On the other hand, it occupies about 10 m of extra length of the transfer line, which is a disadvantage for design of extremely compact medical accelerator complexes fitting to the hospitals.

In addition the entire rotator has to be rotated synchronously with the gantry, which requires an extra equipment for extremely precise mechanical rotation.

Therefore it is the object of the present invention to save space and costs and to avoid such a rotator so that a gantry rotation independent transport of non-symmetric ion beams is possible. Thus, the ion-optical settings should make the beam parameters at the gantry exit independent from the angle of gantry rotation even if the beam enters the gantry with different emittance in horizontal and vertical planes.

This object is achieved by the subject matter of independent claim 1. Features of preferred embodiments are enclosed in dependent claims, depending on claim 1.

Therefore the gantry with an ion-optical system further comprises:
- a horizontal scanner magnet positioned upstream said third bending magnet for horizontal scanning of said ion beam in a plane perpendicular to the beam direction;
- a vertical scanning magnet positioned upstream said third bending magnet for vertical scanning of said ion beam in a plane perpendicular to the beam direction,
- at least six quadrupole magnets with adjustable excitation positioned downstream the said first bending magnet and upstream said scanner magnets, wherein the quadrupole magnets provide:
- a fully achromatic beam transport from the gantry entrance to the isocentre;
- a control of the size of said ion beam in the isocentre according to a pre-defined beam-size pattern; and
- the size of said ion beam in the isocentre and the spot-shape of said ion beam in the isocentre which is independent from the angle of gantry rotation, wherein the gantry can be rotated to any angle between 0° and 360° with respect to a fixed beam transfer line connecting an accelerator with the gantry and wherein said ion beam coming from said fixed beam transfer line and entering said gantry has different emittances in the horizontal and vertical planes of said fixed beam transfer line.

It is a well-known fact that beams of ions (typically $1 \leq Z \leq 8$) have favourable physical and biological properties for their use in cancer-therapy. The most appropriate beam delivery technique, in particular for ions heavier than protons, is a so-called active beam scannig comprising an energy variation from the accelerator and lateral intensity-controlled raster scanning according to the characterising portion of claim 1. In contrast to a passive beam delivery the active scanning systems aim to deliver a narrow pencil-like beam with a variable spot size to the patient and to scan it over the treatment area.

Forming and preservation of the pencil-like beam by the beam transport system is of crucial importance in this case for the ion-optical system of the gantry. The dose-to-target conformity can further be optimised if the beam can enter the patient from any direction. This task is performed by said gantry which is rotated around the horizontal axis with respect to the room, coordinate system. The combination of the pencil-beam scanning with a rotating gantry brings about special additional ion-optical problems.

The beam is described at the exit of the transfer line, at the entrance of the gantry, and at the gantry isocentre by its sigma-matrices $\sigma(0)$, $\sigma(1)$, and $\sigma(2)$, respectively, where the sigma-matrices have, in general, a form:

$$\sigma(i) = \begin{matrix} \sigma(i)_{11} & \sigma(i)_{12} & \sigma(i)_{13} & \sigma(i)_{14} \\ \sigma(i)_{21} & \sigma(i)_{22} & \sigma(i)_{23} & \sigma(i)_{24} \\ \sigma(i)_{31} & \sigma(i)_{32} & \sigma(i)_{33} & \sigma(i)_{34} \\ \sigma(i)_{41} & \sigma(i)_{42} & \sigma(i)_{43} & \sigma(i)_{44} \end{matrix} \quad (1)$$

where i=0, 1, 2 and the individual matrix-terms have their usual meaning. The sigma-matrix is a real positive definite, and symmetric matrix. The square roots of the diagonal terms of the sigma-matrix are a measure of the beam size in x, x', y and y' coordinates, where [x, x', y, y'] is a four-dimensional phase space in which the beam occupies a volume inside a four-dimensional ellipsoid characterised by the sigma-matrix. The off-diagonal terms determine the orientation of the ellipsoid in the phase space. At the exit of the transfer line, a so-called uncoupled beam is expected, i.e. there is no correlation between the two transverse phase spaces [x, x'] and [y, y']. In such a case, the elements of the sigma-matrix coupling the horizontal and vertical phase vanish. Taking into account these properties, the sigma-matrix of the beam at the exit of the transfer line can be written in a simplified form:

$$\sigma(0) = \begin{pmatrix} \sigma(0)_{11} & \sigma(0)_{12} & 0 & 0 \\ \sigma(0)_{12} & \sigma(0)_{22} & 0 & 0 \\ 0 & 0 & \sigma(0)_{33} & \sigma(0)_{34} \\ 0 & 0 & \sigma(0)_{34} & \sigma(0)_{44} \end{pmatrix} \quad (2)$$

If the gantry is rotated with respect to the fixed transfer line by an angle $\alpha$, the sigma-matrix of the beam at the gantry entrance, $\sigma(1)$, will be given by the transformation:

$$\sigma(1) = M_\alpha \cdot \sigma(0) \cdot M_\alpha^T \quad (3)$$

where $M_\alpha^T$ is a transpose matrix to $M_\alpha$ describing the rotation of the coordinate system by an angle a and having a form $$M\alpha = \begin{pmatrix} \cos\alpha & 0 & \sin\alpha & 0 \\ 0 & \cos\alpha & 0 & \sin\alpha \\ -\sin\alpha & 0 & \cos\alpha & 0 \\ 0 & -\sin\alpha & 0 & \cos\alpha \end{pmatrix} \quad (4)$$

The beam transport system of the gantry is characterised by its transfer matrix $M_{GAN}$:

$$M_{GAN} = \begin{pmatrix} r_{11} & r_{12} & 0 & 0 \\ r_{21} & r_{22} & 0 & 0 \\ 0 & 0 & r_{33} & r_{34} \\ 0 & 0 & r_{43} & r_{44} \end{pmatrix} \quad (5)$$

The transfer matrix $M_{GAN}$ must fulfil a condition $\det M_{GAN}=1$ (6). It is already assumed in eq. (5) that there is no coupling between horizontal and vertical planes in the gantry optics itself. The pertinent terms have been set to zero. In addition, the beam transport system of the gantry is assumed to be achromatic in the gantry isocentre. ($D_{ISO}=0$, $D'_{ISO}=0$ (7, 8), where $D_{ISO}$ is the dispersion function at the gantry isocentre), which allows to write the transfer matrix $M_{GAN}$ in a 4×4 form without the terms related to the dispersion function. The sigma-matrix of the beam at the gantry isocentre, $\sigma(2)$, is given by the relation:

$$\sigma(2) = M_{GAN} \cdot \sigma(1) \cdot M_{GAN}^T \quad (9)$$

The achromatic beam transport in the gantry must also be independent from the angle of gantry rotation. This can be achieved, if the dispersion function and its derivative are set to zero at the gantry entrance. This translates to the ion-optical constraints upon the transfer line to form a dispersion-free region at its exit.

Not all beam parameters at the gantry isocentre must be independent from the angle of the gantry rotation. For tumour irradiation, it is enough to achieve an angular independence for the beam size in both transverse planes and for the shape of the beam spot. A round beam spot is required. In the sigma-matrix formalism language, these requirements can be written as:

$$\sigma(2)_{11}=\sigma(2)_{33} \neq f(\alpha) \text{ AND } \sigma(2)_{13}=0 \neq f(\alpha) \quad (10)$$

In addition, the beam size must be adjustable from 4 to 10 mm diameter.

After listing the basic assumptions, we can proceed to investigate a dependence of the beam parameters at the gantry isocentre on the angle of gantry rotation. It is convenient to combine eqs. (3) and (9) in order to express the overall transformation from the exit of the transfer line to the gantry isocentre.

$$\sigma(2) = M_{GAN} \cdot \sigma(1) \cdot M^T_{GAN} = M_{GAN} \cdot M_\alpha \cdot \sigma(0) \cdot M^T_\alpha \cdot M^T_{GAN}$$

$$= M_{OVER} \cdot \sigma(0) \cdot M^T_{OVER} \quad (11)$$

where $M_{OVER}$ is the overall transfer matrix from the exit of the transfer line to the gantry isocentre given by a relation:

$$M_{OVER} = M_{GAN} \cdot M_\alpha \quad (12)$$

Because the matrix $M_\alpha$ contains the terms depending on the angle of gantry rotation $\alpha$ (see eq. (4)), these terms 'penetrate' also to the sigma-matrix of the beam in the gantry isocentre $\sigma(2)$ through the transformation (11). One gets by performing the matrix multiplication (11):

$$\sigma(2)_{11} = r^2_{11} \cdot [\sigma(0)_{11} \cos^2\alpha +$$

$$\sigma(0)_{33} \sin^2\alpha] + 2r_{11}r_{12}\sigma$$

$$(0)_{12} \cos^2\alpha + r^2_{12} \cdot [\sigma(0)_{22} \cos^2\alpha + \sigma$$

$$(0)_{44} \sin^2\alpha] + 2r_{11}r_{12}\sigma(0)_{34} \sin^2\alpha \quad (13)$$

It is interesting to find out that eliminating the $\alpha$-containing terms in eq. (13) is feasible and that there are even several ways to do so. Equation (13) becomes:

$$\sigma(2)_{11} = r^2_{12} \cdot \sigma(0)_{22} \neq f(\alpha) \text{ if}$$

$$r_{11}=0 \text{ AND } \sigma(0)_{22}=\sigma(0)_{44} \quad (14)$$

or $$\sigma(2)_{11} = r^2_{11} \cdot \sigma(0)_{11} \neq f(\alpha) \text{ if}$$

$$r_{12}=0 \text{ AND } \sigma(0)_{11}=\sigma(0)_{33} \quad (15)$$

An identical set of constraints can be obtained in the vertical plane of the gantry:

$$\{r_{33}=0 \text{ AND } \sigma(0)_{22}=\sigma(0)_{44}\} \text{ OR}$$

$$\{r_{34}=0 \text{ AND } \sigma(0)_{11}=\sigma(0)_{33}\} \quad (16)$$

The xy correlation term $\sigma(2)_{13}$ will be:

$$\sigma(2)_{13} = \sin\alpha \cos\alpha \cdot [r_{11}r_{33}(\sigma(0)_{33} - \sigma$$

$$(0)_{11}) + r_{11}r_{34}(\sigma(0)_{34} - \sigma(0)_{12}) +$$

$$r_{12}r_{34}(\sigma(0)_{44} - \sigma(0)_{22}) +$$

$$r_{12}r_{33}(\sigma(0)_{34} - \sigma(0)_{12})] \quad (17)$$

The condition $\sigma(2)_{13}=0 \neq f(\alpha)$ is satisfied if the following constraints are fulfilled:

$$\{r_{11}=0 \text{ AND } r_{33}=0 \text{ AND } \sigma(0)_{22}=\sigma$$

$$(0)_{44}\} \text{ OR } \{r_{12}=0 \text{ AND } r_{34}=0 \text{ AND}$$

$$\sigma(0)_{11}\sigma(0)_{33}\}$$

The logical relations between the above ion-optical constraints are sketched in Tab. 1.

Preferred embodiments and further advantages of the present invention are now described in more detail with respect to the accompanying drawings.

FIG. 2 is a diagram of beam envelopes in the gantry for two significant gantry positions.

FIG. 4 is an illustration of the action of the scanning magnets.

Figure 1:
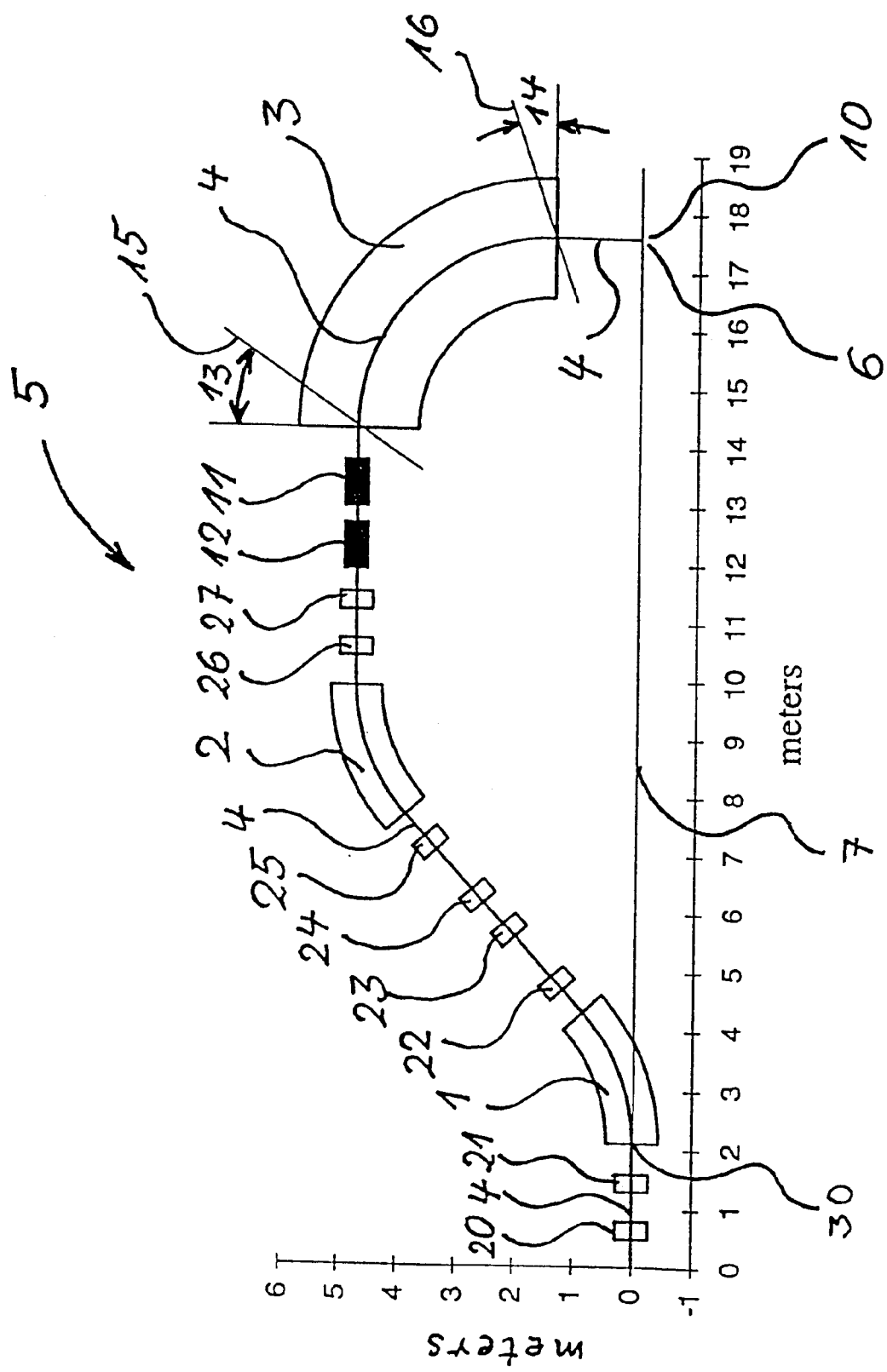
FIG. 1 is a layout of a gantry.

The above matrix analysis was followed by computer simulations. The constraints were applied upon an isocentric normalconducting gantry. Its layout is shown in FIG. 1, wherein the reference numerals 20–27 designates quadrupole magnets, 1 and 2 designates 42° bending magnets as a first and second bending magnet, respectively, 3 designates a 90° bending magnet as a third bending magnet, 4 designates an ion beam, 7 designates an axis of rotation of the gantry 5, 10 designates an isocentre, 30 designates the gantry entrance and 6 designates the intersection of the ion beam 4 and the axis 7 at the isocentre 10, 11 designates a horizontal scanner, 12 designates a vertical scanner, 13 designates an input pole face 15 rotation of 30° and 14 designates an exit pole face 16 rotation of 21°.

The input beam emittances were assumed $\epsilon_x=5\pi$ mm·mrad and $\epsilon_y=1\pi$ mm·mrad in the two transverse planes, momentum spread $\Delta p/p=0.2\%$. The simulations show that it fits the required ion-optical constraints and it achieves a satisfactory beam focusing for an input beam with a small divergence satisfying the condition $\sigma(0)_{22}=\sigma(0)_{44}$ (the left column in Tab. 1). FIGS. 2a and 2b show the beam envelopes 40 and 41 in the gantry 5 for two significant gantry positions differing by the angle of gantry rotation 90°.

FIG. 2a) is a situation when the gantry transports the beam with the minimum emittance in its horizontal plane. FIG. 2b) is a situation when the gantry transports the beam with the minimum emittance in its vertical plane. The reference numerals 20–27 designates quadrupoles, 1 and 2 designates 42° bending magnets, 3 designates a 90° bending magnet, the upper plot 40 designates a horizontal plane of the gantry 5 and the lower plot 41 designates a vertical plane of the gantry and the dashed line 42 designates a dispersion function.

In one position, the horizontal plane of the gantry 5 transports the beam 4 with the maximum emittance, in the other position, the horizontal plane of the gantry 5 transports the beam 4 with the minimum emittance.

Figure 3A:
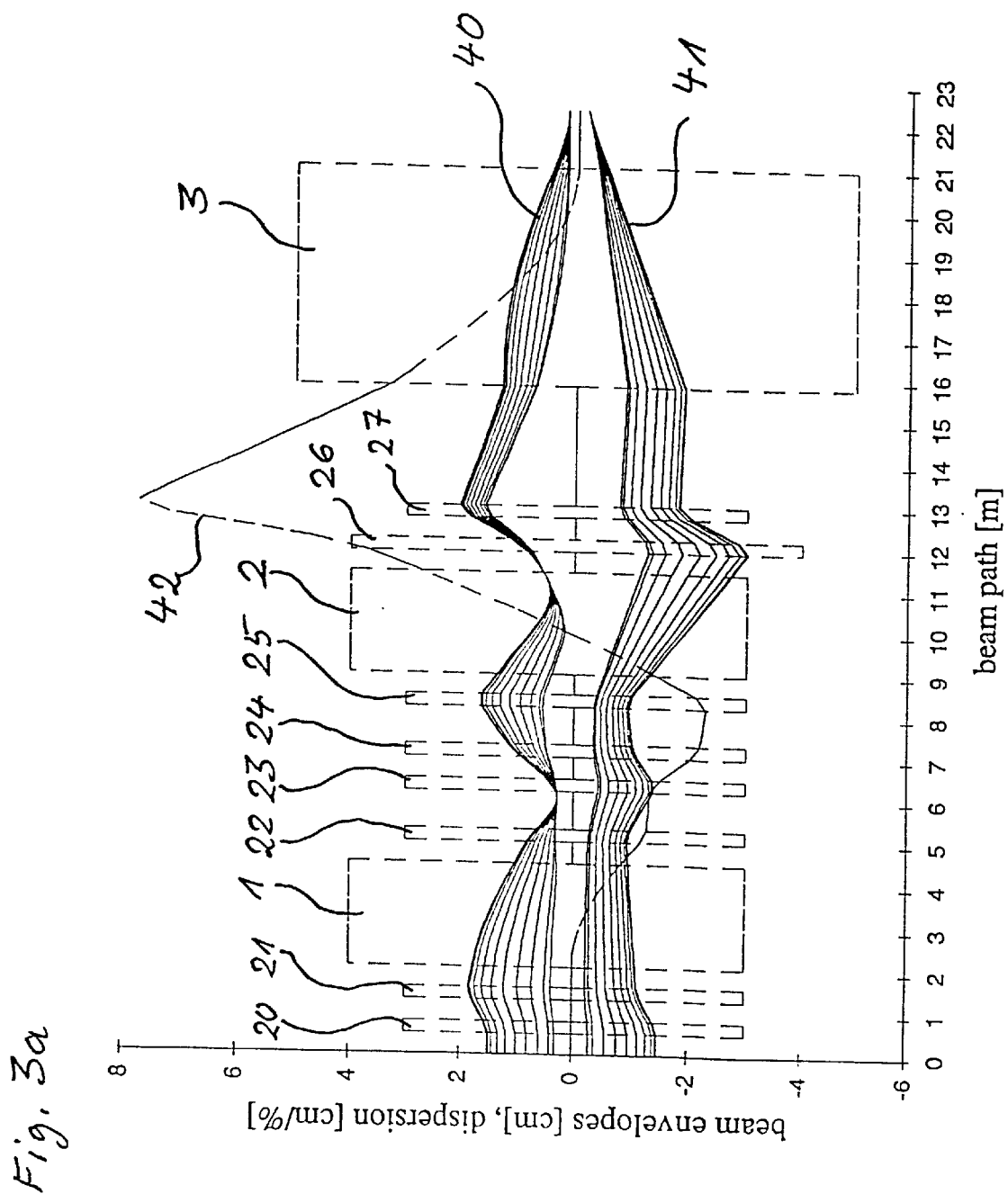
FIG. 3 is a diagram of beam envelopes in the gantry as a function of the angle of gantry rotation.

In order to demonstrate the angular independence of the beam transport, the next FIG. 3 shows in one plot all beam envelopes inbetween these two gantry positions with the 10° increment of the angle of gantry rotation. The plots are shown for a 4 mm output beam (FIG. 3a) and 10 mm output beam (FIG. 3b), $\epsilon_x/\epsilon_y=5$. The ion-optical settings of the gantry corresponding to FIG. 3 are listed in Tab. 2. The reference signs designate the same items as in FIG. 2a and 2b. In order to increase the resolution of the plot, the aperture of the third bending magnet 3 is given out of scale.

The beam size control is done exclusively by the gantry optics without involving the transfer line into this job. It means, that the transfer line forms at its exit always a beam having the same output parameters regardless the beam size required at the gantry isocentre 10. Different settings of the gantry quadrupoles 22–27 are applied to control the beam size at the isocentre 10. Besides two extreme examples shown in FIG. 3, the simulations were done for all beam diameters from 4 to 10 mm in 1 mm steps.

FIG. 4 illustrates the action of the scanning magnets 11 and 12. The scanning magnets 11 and 12 are located upstream to the third bending magnet 3 but downstream to the last quadrupole lens 27. This position was found to be the optimum from the ion-optical point of view. The edge focusing of the entrance and exit pole faces 15, 16 of the third gantry magnet 3 is used to achieve nearly the parallel scanning mode. The deviation from the ideal parallel scanning is 0.2° at the maximum beam displacement of 10 cm. The scanning field is 20×20 cm$^2$. The input and exit pole face rotation angles 13, 14 (shown in FIG. 1) are 30° and 21°, respectively. The upper part of FIG. 4 illustrates the horizontal plane 111 and the beam deflection 50 caused by the horizontal scan 11 shown in the bending range of the third bending magnet 3. The lower part of FIG. 4 illustrates the vertical plane 112 and the beam deflection 60 caused by the vertical scan 12 shown in the bending range of the third bending magnet 3.

The solution of the present invention can be used only with a gantry which is able to satisfy the required ion-optical constraints listed in Tab. 1. Such a gantry must have an appropriate number of variable elements, according to the present invention at least six quadrupole magnets with adjustable excitation. All together, the present invention supports six ion-optical constraints: two for achromatic beam transport, two for getting the rotation independence and two for controlling the beam size. It means that the minimum number of quadrupoles according to the present invention is six. As it can be seen from Tab. 2, a preferred embodiment comprises eight quadrupoles which brings certain redundancy compared to the minimum. However, this redundancy is advantageous for a realistic design of a system in which the variables cannot be set to arbitrary values. The magnetic flux density on the quadrupole pole tips is physically limited (the limit was set to 0.8 T in the preferred embodiment) as well as the beam envelopes inside the gantry should be controlled in such a way that the aperture of the beam transport elements stays as small as possible. Furthermore, the redundancy can be used to minimise the error sensitivity of the beam transport system. Note that eliminating the gantry rotation angle containing terms from the beam parameters at the gantry isocentre by setting the proper terms of the gantry transfer matrix to zero is valid for any emittance differences in the two transverse planes. Actually, it does not depend on the $\epsilon_x/\epsilon_y$ ratio at all. The calculations were done for $\epsilon_x/\epsilon_y=5$ and $\epsilon_x/\epsilon_y=10$, which is much more than the measured values known from the prior art. However, for extremely large emittance ratios one can encounter the problems of getting the equal beam spot sizes at the isocentre, keeping the beam envelopes inside the gantry within a reasonable aperture or forming a suitable beam at the coupling point. These problems occure for $\epsilon_x/\epsilon_y>15$.

It is also an interesting fact of the present invention that only two more ion-optical constraints namely $r_{11}=r_{33}=0$ or $r_{12}=r_{34}=0$ have to be added to the set of gantry constraints to achieve the rotation independent beam transport. The other constraints for achromatic beam transport and beam size control must be fulfilled anyway.

The bending magnets are assumed to use the field up to 2 T. But is might be feasible to reduce the field down to 1.8 T in order to avoid some saturation-related dynamic effects during the ramping of the magnets. However, this change has no influence on the concept of the rotation independent beam transport of the present invention.

It is certainly possible to run a gantry (5) in a mode, when the gantry setting is a function of the angle of gantry rotation. Such a mode would, however, require a large data set storing all settings as a function of the beam size and, in addition to that, as a function of the angle of gantry rotation. There is also a necessity of having different settings as a function of the beam energy and particle species. It is therefore a significant advantage to eliminate the dependence on the angle of gantry rotation, which reduces the amount of data roughly by factor of 100 (90°- one quadrant of the gantry rotation, 1°- angular resolution of gantry position).

TABLE 1

A summary and logical relations between the ion-optical constraints leading to the gantry rotation independent beam transport of non-symmetric beams are shown in Tab. 1. Two possible sets of ion-optical constraints are represented by two columns in Tab. 1. Logical "OR" is applied between these two columns, while logical "AND" holds between the constraints inside a given column.

TRANSFER LINE
always achromatic: $D = 0$ AND $D' = 0$ at the exit of the transfer line GANTRY
always achromatic: $r_{16} = 0$ AND $r_{26} = 0$
$\sigma(0)_{22} = \sigma(0)_{44}$ AND $r_{11} = 0$ AND $r_{33} = 0$
OR
$\sigma(0)_{11} = \sigma(0)_{33}$ AND $r_{12} = 0$ AND $r_{34} = 0$

TABLE 2

The gantry settings corresponding to the rotation independent beam transport shown in FIG. 3 are listed in table 2. The following abbreviations are used: $L_{eff}$ = effective length of the quadrupole, Ap = radius of the quadrupole aperture, B = magnetic flux density on the quadrupole pole tip ("—" for the vertical focusing), $B_{BEND}$ = magnetic flux density of the dipole magnet, IR = input pole face rotation angle, ER = exit pole face rotation angle, d = drift length. All bending magnets are designed without the field gradient, i.e. N = 0.

| | | Settings | |
|---|---|---|---|
| Element | Physical parameters | 4 mm beam | 10 beam |
| Drift | d = 0.5 m | | |
| Quadrupole | $L_{eff}$ = 0.3 m Ap = 3 cm | B = −0.194 T | B = −0.364 T |
| Drift | d = 0.5 m | | |
| Quadrupole | $L_{eff}$ = 0.3 m Ap = 3 cm | B = +0.210 T | B = +0.490 T |
| Drift | d = 0.5 m | | |
| 42° Bending Magnet | $B_{BEND}$ = 2 T IR = 0° ER = 0° | | |
| Drift | d = 0.5 m | | |
| Quadrupole | $L_{eff}$ = 0.3 m Ap = 3 cm | B = +0.318 T | B = +0.751 T |
| Drift | d = 0.9 m | | |
| Quadrupole | $L_{eff}$ = 0.3 m Ap = 3 cm | B = +0.445 T | B = +0.211 T |
| Drift | d = 0.5 m | | |
| Quadrupole | $L_{eff}$ = 0.3 m Ap = 3 cm | B = +0.281 T | B = −0.066 T |
| Drift | d = 0.9 m | | |

TABLE 2-continued

The gantry settings corresponding to the rotation independent beam transport shown in FIG. 3 are listed in table 2. The following abbreviations are used: $L_{eff}$ = effective length of the quadrupole, Ap = radius of the quadrupole aperture, B = magnetic flux density on the quadrupole pole tip ("—" for the vertical focusing), $B_{BEND}$ = magnetic flux density of the dipole magnet, IR = input pole face rotation angle, ER = exit pole face rotation angle, d = drift length. All bending magnets are designed without the field gradient, i.e. N = 0.

| | | Settings | |
|---|---|---|---|
| Element | Physical parameters | 4 mm beam | 10 beam |
| Quadrupole | $L_{eff}$ = 0.3 m Ap = 3 cm | B = +0.426 T | B = −0.252 T |
| Drift | d = 0.5 m | | |
| 42° Bending Magnet | $B_{BEND}$ = 2 T IR = 0° ER = 0° | | |
| Drift | d = 0.5 m | | |
| Quadrupole | $L_{eff}$ = 0.3 m Ap = 4 cm | B = −0.643 T | B = −0.109 T |
| Drift | d = 0.5 m | | |
| Quadrupole | $L_{eff}$ = 0.3 m Ap = 3 cm | B = +0.567 T | B = +0.307 T |
| Drift for the scanning system | d = 2.8 m | | |
| 90° Bending Magnet | $B_{BEND}$ = 2 T IR = +30° ER = +21° | | |
| Drift to the patient | d = 1.4 m | | |

What is claimed is:

1. Gantry with an ion-optical system comprising:

a first bending magnet (1) with a bending angle in the range of 40° to 45° for bending an ion beam (4) off an axis (7) of rotation of said gantry;

a second bending magnet (2) with a bending angle identical to the bending angle of the first bending magnet (1) for bending said ion beam (4) parallel to said axis (7) of rotation of said gantry (5);

a third bending magnet (3) with a bending angle in the range of 45° to 90° for bending said ion beam (4) toward an intersection (6) of said ion beam (4) with said axis (7) of gantry (5) rotation, wherein the intersection (6) point is called the isocentre (10); characterized in that said gantry further comprises a horizontal scanner magnet (11) positioned upstream said third bending magnet (3) for horizontal scanning of said ion beam (4) in a plane perpendicular to the beam direction;

a vertical scanning magnet (12) positioned upstream said third bending magnet (3) for vertical scanning of said ion beam (4) in a plane perpendicular to the beam direction;

at least six quadrupole magnets (22–27) with adjustable excitation positioned downstream to said first bending magnet (1) and upstream said scanning magnets (11, 12), wherein the quadrupole magnets provide:

a fully achromatic beam transport from the gantry entrance (30) to the isocentre (10);

a control of the size of said ion beam (4) in the isocentre (10) according to a pre-defined beam-size pattern; and the size of said ion beam (4) in the isocentre (10) and the spot-shape of said ion beam (4) in the isocentre (10) which is independent from the angle of gantry (5) rotation, wherein the gantry (5) can be rotated by any angle between 0° and 360° with respect to a fixed beam transfer line connecting an accelerator with the gantry (5) and wherein said ion beam (4) coming from said fixed beam transfer line and entering said gantry (5) has different emittances in the horizontal and vertical planes of said fixed beam transfer line.

2. Gantry according to claim 1, characterized in that magnetic rigidity of transport of said ion beam (4) ranges at least from 1.1 to 6.6 Tm for said adjustable excitation.

3. Gantry according to claim 1, characterized in that at least two additional quadrupoles (20, 21) are positioned upstream the first bending magnet (1) for minimizing the error sensitivity of the beam transport system.

* * * * *